US009090736B2

(12) United States Patent
Schwalm et al.

(10) Patent No.: US 9,090,736 B2
(45) Date of Patent: Jul. 28, 2015

(54) RHEOLOGICAL AGENT FOR RADIATION-CURABLE COATING COMPOSITIONS

(75) Inventors: Reinhold Schwalm, Wachenheim (DE); Erich Beck, Ladenburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/399,006

(22) Filed: Feb. 17, 2012

(65) Prior Publication Data

US 2012/0214894 A1    Aug. 23, 2012

Related U.S. Application Data

(60) Provisional application No. 61/445,096, filed on Feb. 22, 2011.

(51) Int. Cl.
| | |
|---|---|
| C08G 18/78 | (2006.01) |
| C08G 18/67 | (2006.01) |
| C08G 18/81 | (2006.01) |
| C08F 283/00 | (2006.01) |
| C08K 5/21 | (2006.01) |
| C09D 175/14 | (2006.01) |
| C09D 175/16 | (2006.01) |
| C07C 275/04 | (2006.01) |
| C07C 275/26 | (2006.01) |
| C07C 275/60 | (2006.01) |

(52) U.S. Cl.
CPC .......... *C08G 18/8116* (2013.01); *C07C 275/04* (2013.01); *C07C 275/26* (2013.01); *C07C 275/60* (2013.01); *C08F 283/008* (2013.01); *C08G 18/671* (2013.01); *C08G 18/672* (2013.01); *C08G 18/673* (2013.01); *C08G 18/675* (2013.01); *C08G 18/6705* (2013.01); *C08G 18/7837* (2013.01); *C08G 18/8125* (2013.01); *C08K 5/21* (2013.01); *C09D 175/14* (2013.01); *C09D 175/16* (2013.01)

(58) Field of Classification Search
USPC ............ 528/49, 75; 560/24, 32, 33, 115, 157, 560/163, 164, 165, 166; 564/32, 56
IPC .. C07C 275/04,275/26, 275/60; C08F 283/008; C08G 18/6705, 18/671, 18/672, 18/673, 18/675, C08G 18/7837, 18/8116, 18/8125; C08K 5/21; C09D 175/14, 175/16
See application file for complete search history.

(56) References Cited

U.S. PATENT DOCUMENTS

| | | | |
|---|---|---|---|
| 4,311,622 A | 1/1982 | Buter | |
| 4,540,734 A | 9/1985 | Short et al. | |
| 4,596,678 A | 6/1986 | Merger et al. | |
| 4,596,679 A | 6/1986 | Hellbach et al. | |
| 4,965,317 A | 10/1990 | Kania et al. | |
| 5,087,739 A | 2/1992 | Bohmholdt et al. | |
| 5,093,411 A * | 3/1992 | Buter | 524/761 |
| 6,617,413 B1 * | 9/2003 | Bruchmann et al. | 528/75 |
| 7,576,151 B2 | 8/2009 | Brinkhuis et al. | |
| 2006/0009589 A1 | 1/2006 | Haering et al. | |
| 2010/0022797 A1 * | 1/2010 | Henninger et al. | 560/336 |

FOREIGN PATENT DOCUMENTS

| | | |
|---|---|---|
| DE | 33 16 593 A1 | 11/1984 |
| DE | 198 26 712 A1 | 12/1999 |
| DE | 199 13 353 A1 | 9/2000 |
| DE | 199 57 900 A1 | 6/2001 |
| DE | 100 13 186 A1 | 9/2001 |
| DE | 100 13 187 A1 | 10/2001 |
| EP | 0 054 105 A1 | 6/1982 |
| EP | 0 092 269 A1 | 10/1983 |
| EP | 0 126 299 A1 | 11/1984 |
| EP | 0 126 300 A1 | 11/1984 |
| EP | 0 192 304 A1 | 8/1986 |
| EP | 0 198 519 A1 | 10/1986 |
| EP | 0 279 303 A2 | 8/1988 |
| EP | 0 355 443 A2 | 2/1990 |
| EP | 0 680 985 A1 | 11/1995 |
| WO | WO 98/33761 | 8/1998 |
| WO | WO 00/39183 | 7/2000 |
| WO | WO 02/064684 A2 | 8/2002 |
| WO | WO 2005/005558 A1 | 1/2005 |
| WO | WO 2006/005491 A1 | 1/2006 |

OTHER PUBLICATIONS

Laromer LR 9000 Technical Data Sheet; BASF Corporation; Mar. 2010; pp. 1-3.*

* cited by examiner

*Primary Examiner* — Rabon Sergent
(74) *Attorney, Agent, or Firm* — Servilla Whitney LLC

(57) ABSTRACT

A radiation-curable rheological assistant which comprises a compound comprising at least one (meth)acrylate group and at least one urea group of the formula —NH—(CO)—NR$^1$R$^2$ connected thereto wherein R$^1$ and R$^2$ each independently of one another are hydrogen, alkyl, aryl, cycloalkyl or aralkyl, with the proviso that at least one of the radicals is other than hydrogen, a process for preparing the rheological assistant by reacting at least one compound which has at least one isocyanate-reactive group and at least one (meth)acrylate group with at least one di- or polyisocyanate, use of the rheological assistant in radiation-curable coating compositions, such radiation-curable coating compositions, and the use of such radiation-curable coating compositions.

15 Claims, No Drawings

RHEOLOGICAL AGENT FOR RADIATION-CURABLE COATING COMPOSITIONS

The present invention relates to new, radiation-curable compounds, to their use in radiation-curable coating compositions, to such radiation-curable coating compositions, and to the use of the new, radiation-curable compounds as rheological agents in radiation-curable coating compositions.

In the application of coatings, especially by means of spray application, the formulations used must be of relatively low viscosity. The low viscosity of the formulations causes difficulties especially when the components to be coated are vertical, since in this case the coatings sag and hence the film thickness distribution over the component is not uniform. These problems are relatively minor in the case of aqueous formulations or those of high solvent content, since the viscosity increases significantly through the evaporation of the solvent or water on application.

In the case of solvent borne coating materials with a high solids content, and more particularly in the case of 100% coating materials which are UV curable, there is virtually no perceptible increase in viscosity. As a consequence, the rheological assistants that are conventionally employed (thickeners or sag control agents) are effective hardly at all or only at high concentrations.

Since high concentrations of auxiliaries, particularly in UV-curable coating materials, have the effect of lowering the network density, there is a need for improved rheological assistants or for assistants which do not significantly negatively impact the network density.

Rheological assistants obtainable by reacting an isocyanate with an amine to form a urea are already known.

WO 2005/005558 (=U.S. Pat. No. 7,576,151) describes the reaction of polyisocyanates with amino acid esters.

U.S. Pat. No. 4,311,622, EP 198519, and EP 192304 describe the preferably stoichiometric reaction of isocyanates with monoamines, including benzylamine, and the use of the resultant products as rheological assistants.

A disadvantage is that these rheological assistants, as observed above, lower the network density in the case of radiation-curable coating compositions.

U.S. Pat. No. 4,965,317 describes rheological assistants which are obtained by copolymerization of free-radically polymerizable monomers with monomers containing isocyanate groups and/or with subsequent modification with isocyanate groups.

U.S. Pat. No. 4,540,734 describes rheological assistants for which first of all a prepolymer containing isocyanate groups is prepared, which is subsequently reacted with ethanolamines to form a urea-terminated rheological assistant.

WO 02/064684 describes rheological assistants which are the products of the reaction of isocyanates with amines.

None of the documents solves the problem of the lowering of network density on deployment in radiation-curable coating compositions.

The object is achieved by means of rheological assistants comprising
at least one (meth)acrylate group and connected thereto
at least one urea group of the formula (I)

—NH—(CO)—NR$^1$R$^2$ in which
R$^1$ and R$^2$ each independently of one another are hydrogen, alkyl, aryl, cycloalkyl or aralkyl, with the proviso that at least one of the radicals is other than hydrogen.

In one preferred embodiment, at least one, preferably precisely one, of the two radicals R$^1$ and R$^2$ is a radical of the formula (II)

—R$^3$—R$^4$, in which
R$^3$ is C$_1$ to C$_{10}$ alkylene, preferably C$_1$ to C$_4$ alkylene, more preferably C$_1$ to C$_2$ alkylene, and very preferably methylene, and
R$^4$ is optionally substituted, preferably unsubstituted, C$_6$ to C$_{12}$ aryl.

In one particularly preferred embodiment, one of the radicals R$^1$ and R$^2$ is hydrogen and one is a radical of the formula (II).

By an alkyl radical in the context of this specification is meant an aliphatic, open-chain, branched or unbranched hydrocarbon radical having 1 to 20 carbon atoms, preferably 1 to 10, more preferably 1 to 8, and very preferably 1 to 4 carbon atoms.

Examples of alkyl radicals are methyl, ethyl, isopropyl, n-propyl, n-butyl, isobutyl, sec-butyl, tert-butyl, n-hexyl, n-heptyl, 2-ethylhexyl, 2-propylheptyl, n-octyl, n-decyl, n-dodecyl, n-tetradecyl, n-hexadecyl, n-octadecyl, and n-eicosyl. Preferred alkyl radicals are methyl, ethyl, isopropyl, n-propyl, n-butyl, isobutyl, sec-butyl, tert-butyl, n-hexyl, n-heptyl, 2-ethylhexyl, 2-propylheptyl, particular preference being given to methyl, ethyl, isopropyl, n-propyl, n-butyl, isobutyl, sec-butyl, and ted-butyl, and very particular preference to methyl, ethyl, isopropyl, n-butyl, and ted-butyl.

By an aryl radical in the context of this specification is meant an aromatic, optionally substituted ring system containing 6 to 12 carbon atoms, preferably a ring system containing 6 to 12 carbon atoms which is optionally substituted by aryl, alkyl, aryloxy, alkyloxy, heteroatoms and/or heterocycles.

Examples thereof are phenyl, tolyl, xylyl, α-naphthyl, β-naphthyl, fluorenyl, 4-biphenylyl, chlorophenyl, dichlorophenyl, trichlorophenyl, difluorophenyl, methylphenyl, dimethylphenyl, trimethylphenyl, ethylphenyl, diethylphenyl, iscpropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl. Preference is given to phenyl, tolyl, α-naphthyl, β-naphthyl, and fluorenyl, particular preference to phenyl, β-naphthyl, and fluorenyl, and very particular preference to phenyl.

By cycloalkyl is meant in the context of this specification C$_5$-C$_{12}$ cycloalkyl which is optionally substituted by aryl, alkyl, aryloxy, alkyloxy, heteroatoms and/or heterocycles, examples being cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, and dichlorocyclopentyl, and also a saturated or unsaturated bicyclic system such as norbornyl or norbornenyl, for example. The cycloalkyl is preferably not substituted.

Preferred cycloalkyl is cyclopentyl, cyclohexyl, cyclooctyl, or cyclododecyl, more preferably cyclopentyl, or cyclohexyl.

By an aralkyl is meant in the context of this specification an alkyl radical which is substituted by one or more, preferably precisely one, aryl radical. The aryl radical preferably has 6 to 12 carbon atoms and the alkyl radical preferably has 1 to 6, more preferably 1 to 4, very preferably 1 to 2, and more particularly precisely one carbon atoms.

Examples of aralkyl are benzyl, 2-phenylethyl, 2-phenylpropyl, and 2-phenylprop-2-yl, preferably benzyl, and 2-phenylethyl, more preferably benzyl.

$C_1$ to $C_{10}$ alkylene, preferably $C_1$ to $C_4$ alkylene, more preferably $C_1$ to $C_2$ alkylene is, for example, methylene, 1,2-ethylene, 1,2- or 1,3-propylene, 1,2-, 1,3- or 1,4-butylene, 1,6-hexylene, 1,8-octylene, 1,1-dimethyl-1,2-ethylene or 1,2-dimethyl-1,2-ethylene.

One preferred possibility for preparing such rheological assistants lies in the synthesis of a polyurethane(meth)acrylate (A) by reacting at least one compound which has at least one, preferably precisely one, isocyanate-reactive group and at least one (meth)acrylate group with at least one di- or polyisocyanate and optionally further synthesis components in such a way that there remains at least one free isocyanate group on average per molecule, and reacting this at least one free isocyanate group with an amine of the formula (III)

$H-NR^1R^2$.

Particularly preferred radiation-curable polyurethane (meth)acrylates (A) are synthesized from (a1) at least one aliphatic and/or cycloaliphatic diisocyanate and/or at least one polyisocyanate based on aliphatic and/or cycloaliphatic diisocyanates, (a2) at least one compound having at least one, preferably precisely one, group reactive toward isocyanate groups, and at least one free-radically polymerizable C=C double bond, (a3) optionally at least one compound having at least two groups reactive toward isocyanate groups and selected from hydroxyl, mercapto, primary and/or secondary amino groups, having a number-average molar weight Mn of not more than 500 g/mol, (a4) optionally at least one compound having at least two groups reactive toward isocyanate groups and selected from hydroxyl, mercapto, primary and/or secondary amino groups, having a number-average molar weight Mn of more than 500 g/mol, (a5) at least one amine of the formula (III)

$H-NR^1R^2$, and also (a6) optionally at least one compound which is different from (a2) and (a5) and which has precisely one group reactive toward isocyanate groups, and also (a7) optionally at least one polyisocyanate different from (a1).

In the compounds (A) it is preferred not to use compounds containing isocyanate groups some or all of which have been reacted with what are known as blocking agents. By blocking agents in this context are meant compounds which convert isocyanate groups into blocked (capped or protected) isocyanate groups, which then, below a temperature referred to as the deblocking temperature, do not display the typical reactions of a free isocyanate group. Compounds of this kind with blocked isocyanate groups, that are preferably not used in accordance with the invention, are typically employed in dual-cure coating materials which are cured to completion via isocyanate group curing. Following their preparation, the polyurethanes of the invention preferably have substantially no free isocyanate groups any longer, in other words containing in general less than 1% by weight of NCO, more preferably less than 0.75%, very preferably less than 0.66%, and with particular preference less than 0.3% by weight of NCO (calculated with a molar weight of 42 g/mol).

Components (a1)

Particularly suitable polyisocyanates as components (a1) for the polyurethanes of the invention are polyisocyanates based on (cyclo)aliphatic diisocyanates. As component (a1), additionally, (cyclo)aliphatic diisocyanates are suitable.

The term (cyclo)aliphatic is an abbreviation in this specification for cycloaliphatic or aliphatic.

Cycloaliphatic isocyanates are those which comprise at least one cycloaliphatic ring system.

Aliphatic isocyanates are those which comprise exclusively linear or branched chains, i.e., acyclic compounds.

The polyisocyanates which can be used in accordance with the invention contain no aromatic groups.

The monomeric isocyanates are preferably diisocyanates which carry just two isocyanate groups. It would also be possible in principle, however, for them to be monoisocyanates with one isocyanate group; such compounds, however, are less preferred.

Also suitable in principle are higher isocyanates containing on average more than 2 isocyanate groups; these, however, are less preferred. Suitability therefor is possessed, for example, by triisocyanates such as triisocyanatononane or 2'-isocyanatoethyl 2,6-diisocyanatohexanoate, or the mixtures of di-, tri-, and higher polyisocyanates.

The monomeric isocyanates contain substantially no reaction products of the isocyanate groups with themselves.

The monomeric isocyanates are preferably isocyanates having 4 to 20 C atoms. Examples of typical aliphatic diisocyanates are tetramethylene diisocyanate, 1,5-pentamethylene diisocyanate, hexamethylene diisocyanate(1,6-diisocyanatohexane), octamethylene diisocyanate, decamethylene diisocyanate, dodecamethylene diisocyanate, tetradecamethylene diisocyanate, derivatives of lysine diisocyanate, (e.g., methyl or ethyl 2,6-diisocyanatohexanoate), trimethylhexane diisocyanate or tetramethylhexane diisocyanate. Examples of cycloaliphatic diisocyanates are 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)-cyclohexane(isophorone diisocyanate), 1,3- or 1,4-bis(isocyanatomethyl)cyclohexane or 2,4-, or 2,6-diisocyanato-1-methylcyclohexane, and also 3 (or 4), 8 (or 9)-bis(isocyanatomethyl)-tricyclo[5.2.1.0$^{2,6}$]decane isomer mixtures.

Particularly preferred diisocyanates are 1,6-hexamethylene diisocyanate, 1,3-bis(isocyanato-methyl)cyclohexane, and isophorone diisocyanate; very particular preference is given to isophorone diisocyanate and 1,6-hexamethylene diisocyanate, with more particular preference being given to isophorone diisocyanate.

It is also possible for mixtures of the stated isocyanates to be present.

Isophorone diisocyanate usually takes the form of a mixture, more particularly a mixture of the cis and trans isomers, generally in a ratio of around 60:40 to 80:20 (w/w), preferably in a ratio of around 70:30 to 75:25, more preferably in a ratio of around 75:25.

The amount of isomeric compounds in the diisocyanate is not critical to the process of the invention. Thus 1,6-hexamethylene diisocyanate may comprise, for example, a small fraction of 2- and/or 3-methyl-1,5-pentamethylene diisocyanate.

For the present invention it is possible to use polyisocyanates not only based on those diisocyanates obtained by phosgenating the corresponding amines, but also those prepared without the use of phosgene, i.e., by phosgene-free processes.

According to EP-A-0 126 299 (U.S. Pat. No. 4,596,678), EP-A-126 300 (U.S. Pat. No. 4,596,679), and EP-A-355 443 (U.S. Pat. No. 5,087,739), for example, (cyclo)aliphatic diisocyanates, such as 1,6-hexamethylene diisocyanate (HDI), can be prepared by reacting the (cyclo)aliphatic diamines with, for example, urea and alcohols to form (cyclo) aliphatic biscarbamic esters, and cleaving them thermally to give the corresponding diisocyanates and alcohols. The synthesis takes place, usually, continuously in a circulation process, and in the presence or absence of N-unsubstituted carbamic esters, dialkyl carbonates, and other byproducts recycled from the reaction process. Diisocyanates obtained in this way generally have a very low, or even unmeasurable, fraction of chlorinated compounds, which can lead to advantageous color numbers in the products. It is a further advantage of the present invention that the process of the invention is based on aliphatic diisocyanates and is independent of their preparation, i.e., independent of whether the preparation is via a phosgenation or via a phosgene-free process.

In one embodiment of the present invention the diisocyanate has a total hydrolyzable chlorine content of less than 200 ppm, preferably of less than 120 ppm, more preferably less than 80 ppm, very preferably less than 50 ppm, more particularly less than 15 ppm, and especially less than 10 ppm. This may be measured, for example, by the ASTM specification D4663-98. It is also, however, possible of course to use diisocyanates having a higher chlorine content, of up to 500 ppm, for example.

It will be appreciated that it is also possible to use mixtures of diisocyanate obtained by reacting the corresponding diamine with, for example, urea and alcohols, and cleaving the resultant biscarbamic esters, with diisocyanate obtained by phosgenating the corresponding amine.

The polyisocyanates based on these diisocyanates are preferably the following compounds:

1) Polyisocyanates containing isocyanurate groups and derived from aliphatic and/or cycloaliphatic diisocyanates. Particularly preferred here are the corresponding aliphatic and/or cycloaliphatic isocyanato-isocyanurates, and more particularly those based on hexamethylene diisocyanate and/or isophorone diisocyanate. The isocyanurates present in this case are more particularly tris-isocyanatoalkyl and/or tris-isocyanatocycloalkyl isocyanurates, which represent cyclic trimers of the diisocyanates, or are mixtures with their higher homologs containing more than one isocyanurate ring. The isocyanato-isocyanurates generally have an NCO content of 10% to 30% by weight, more particularly 15% to 25% by weight, and an average NCO functionality of 2.6 to 8.

2) Polyisocyanates containing uretdione groups and having aliphatically and/or cycloaliphatically attached isocyanate groups, preferably aliphatically and/or cycloaliphatically attached groups, and more particularly those derived from hexamethylene diisocyanate or isophorone diisocyanate. Uretdione diisocyanates are cyclic dimerization products of diisocyanates.

In the context of this invention, the polyisocyanates containing uretdione groups are obtained in a mixture with other polyisocyanates, more particularly those specified under 1). For that purpose, the diisocyanates may be reacted under conditions in which not only uretdione groups but also the other polyisocyanates are formed, or first of all the uretdione groups are formed and then are reacted to give the other polyisocyanates, or the diisocyanates are first reacted to give the other polyisocyanates, which are then reacted to form products containing uretdione groups.

3) Polyisocyanates containing urethane and/or allophanate groups and having aliphatically or cycloaliphatically attached isocyanate groups, as are obtained, for example, by reacting excess amounts of diisocyanate, such as hexamethylene diisocyanate or isophorone diisocyanate, for example, with monohydric or polyhydric alcohols. These polyisocyanates containing urethane and/or allophanate groups generally have an NCO content of 12% to 24% by weight and an average NCO functionality of 2.1 to 4.5. Polyisocyanates of this kind containing urethane and/or allophanate groups may be prepared without catalysis or, preferably, in the presence of catalysts, such as, for example, ammonium carboxylates or ammonium hydroxides, or allophanatization catalysts, e.g., Zn(II) compounds, in each case in the presence of monohydric, dihydric or polyhydric, preferably monohydric, alcohols. The polyisocyanates containing urethane and/or allophanate groups may also be prepared in a mixture with other polyisocyanates, more particularly those specified under 1).

4) Uretonimine-modified polyisocyanates.

5) Carbodiimide-modified polyisocyanates.

6) Hyperbranched polyisocyanates, of the kind known, for example, from DE-A1 10013186 or DE-A1 10013187.

7) Polyurethane-polyisocyanate prepolymers, from di- and/or polyisocyanates with alcohols.

8) Polyurea-polyisocyanate prepolymers.

9) Hydrophilically modified polyisocyanates, i.e., polyisocyanates which in addition to the groups described under 1-10 comprise those groups which are formed formally by addition of molecules with NCO-reactive groups and hydrophilicizing groups onto the isocyanate groups of above molecules. The latter groups are nonionic groups such as alkylpolyethylene oxide and/or ionic groups, derived, for example, from phosphoric acid, phosphonic acid, sulfuric acid or sulfonic acid, and/or their salts.

10) Polyisocyanates comprising iminooxadiazinedione groups, derived preferably from hexamethylene diisocyanate or isophorone diisocyanate. Polyisocyanates of this kind comprising iminooxadiazinedione groups are preparable from diisocyanates by means of specific catalysts.

In preferred compounds (a1) the polyisocyanate comprises at least one moiety selected from the group consisting of isocyanurates, biurets, and allophanates, preferably from the group consisting of isocyanurates and allophanates, as described in WO 00/39183, which is hereby considered by reference to be part of the present disclosure; with particular preference the compound in question is a polyisocyanate containing isocyanurate groups.

In one particularly preferred embodiment the polyisocyanate (a1) is a polyisocyanate based on 1,6-hexamethylene diisocyanate and/or isophorone diisocyanate, very preferably based on isophorone diisocyanate.

More particularly the compound (a1) is a polyisocyanate which comprises isocyanurate groups and is based on 1,6-hexamethylene diisocyanate.

In another preferred embodiment the polyisocyanates (a1) are polyisocyanates containing allophanate groups, in which at least some of the components (a2) are attached via allophanate groups, as described in WO 00/39183. With particular preference the compounds in question are polyisocyanates based on 1,6-hexamethylene diisocyanate.

Components (a2)

Components (a2) are at least one, for example one to three, preferably one to two, and very preferably precisely one compound having at least one, preferably precisely one, group reactive toward isocyanate groups, and at least one, preferably one to three, more preferably one to two, and very preferably precisely one free-radically polymerizable C=C double bond.

Preferred compounds of components (a2) are, for example, the esters of dihydric or polyhydric alcohols with α,β-ethylenically unsaturated monocarboxylic and/or dicarboxylic acids and their anhydrides. Examples of α,β-ethylenically unsaturated monocarboxylic and/or dicarboxylic acids and their anhydrides that can be used include acrylic acid, methacrylic acid, fumaric acid, maleic acid, maleic anhydride, crotonic acid, itaconic acid, etc. Preference is given to using acrylic acid and methacrylic acid, more preferably acrylic acid.

Suitable alcohols are, for example, diols such as ethylene glycol, 1,2-propanediol, 1,3-propanediol, 1,1-dimethylethane-1,2-diol, 2-butyl-2-ethyl-1,3-propanediol, 2-ethyl-1,3-propanediol, 2-methyl-1,3-propanediol, neopentylglycol, neopentylglycol hydroxypivalate, 1,2-, 1,3- or 1,4-butanediol, 1,6-hexanediol, 1,10-decanediol, bis-(4-hydroxycyclohexane)isopropylidene, tetramethylcyclobutanediol, 1,2-, 1,3- or 1,4-cyclohexanediol, cyclooctanediol, norbornanediol, pinanediol, decalindiol, 2-ethyl-1,3-hexanediol, 2,4-diethyloctane-1,3-diol, hydroquinone, bisphenol A, bisphenol F, bisphenol B, bisphenol S, 2,2-bis(4-hydroxycyclohexyl)propane, 1,1-, 1,2-, 1,3-, and 1,4-cyclohexanedimethanol, 1,2-, 1,3- or 1,4-cyclohexanediol, and tricyclodecanedimethanol.

Suitable triols and polyols have, for example, 3 to 25, preferably 3 to 18, carbon atoms. They include, for example trimethylolbutane, trimethylolpropane, trimethylolethane, pentaerythritol, glycerol, ditrimethylolpropane, dipentaerythritol, ditrimethylolpropane, sorbitol, mannitol, diglycerol, threitol, erythritol, adonitol (ribitol), arabitol (lyxitol), xylitol, dulcitol (galactitol), maltitol or isomalt.

Preferably the compounds of components (a2) are selected from 2-hydroxyethyl acrylate, 2-hydroxyethyl methacrylate, 2-hydroxypropyl acrylate, 2-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, trimethylolpropane mono- or -diacrylate, pentaerythritol diacrylate or triacrylate, dipentaerythritol pentaacrylate, and mixtures thereof. Preferred in particular as compounds (a2) are 2-hydroxyethyl acrylate, 2-hydroxyethyl methacrylate, 2-hydroxypropyl acrylate, 2-hydroxypropyl methacrylate, pentaerythritol triacrylate, and dipentaerythritol pentaacrylate.

Preferred compounds (a2) are 2-hydroxyethyl acrylate, 2-hydroxyethyl methacrylate, 2-hydroxypropyl acrylate, 2-hydroxypropyl methacrylate, and pentaerythritol triacrylate; particular preference is given to 2-hydroxyethyl acrylate and pentaerythritol triacrylate, and very particular preference to 2-hydroxyethyl acrylate.

Components a3)

The optional components a3) comprise at least one compound having at least two groups reactive toward isocyanate groups and selected from hydroxyl, mercapto, primary and/or secondary amino groups, preferably hydroxyl and primary amino groups, more preferably hydroxyl groups.

Low molecular weight alcohols a3) have a molecular weight of not more than 500 g/mol. Particularly preferred are alcohols having 2 to 20 carbon atoms and, for example, 2 to 6 hydroxyl groups, preferably 2 to 4, more preferably 2 to 3, and very preferably just 2 hydroxyl groups. Preference is given in particular to hydrolysis-stable short-chain diols having 4 to 20, preferably 6 to 12, carbon atoms. These include preferably 1,1-, 1,2-, 1,3- or 1,4-di(hydroxymethyl)cyclohexane, 2,2-bis(4'-hydroxycyclohexyl)propane, 1,2-, 1,3- or 1,4-cyclohexanediol, tetramethylcyclobutanediol, cyclooctanediol or norbornanediol. Particular preference is given to using aliphatic hydrocarbon-diols, such as the isomeric butanediols, pentanediols, hexanediols, heptanediols, octanediols, nonanediols, decanediols, undecanediols, and dodecanediols. Particular preference is given to 1,2-, 1,3- or 1,4-butanediol, 1,4-pentanediol, 1,5-pentanediol, 1,6-hexanediol, 2,5-hexanediol, di(hydroxymethyl)cyclohexane isomers and 2,2-bis(4'-hydroxycyclohexyl)propane. With very particular preference the diols (a3) are cycloaliphatic diols, more particularly 1,1-, 1,2-, 1,3- or 1,4-di(hydroxymethyl)cyclohexane, 2,2-bis(4'-hydroxycyclohexyl)propane, 1,2-, 1,3- or 1,4-cyclohexanediol.

Components a4)

Suitable compounds a4) are also polymeric polyols. The number-average molecular weight $M_n$ of these polymers is preferably in a range from about 500 to 100 000, more preferably 500 to 10 000. The OH numbers are situated preferably in a range from about 20 to 300 mg KOH/g polymer.

Preferred compounds a4) are polyesterols, polyetherols, and polycarbonate polyols, more preferably polyesterols and polyetherols, and very preferably polyesterols.

Preferred polyesterols are those based on aliphatic, cycloaliphatic and/or aromatic dicarboxylic, tricarboxylic and/or polycarboxylic acids with diols, triols and/or polyols, and also lactone-based polyesterols.

Polyesterpolyols are known, for example, from Ullmanns Encyklopädie der technischen Chemie, 4th edition, volume 19, pp. 62 to 65. Preference is given to using polyesterpolyols obtained by reaction of dihydric alcohols with dibasic carboxylic acids. Instead of the free polycarboxylic acids it is also possible to use the corresponding polycarboxylic anhydrides or corresponding polycarboxylic esters of lower alcohols or mixtures thereof to prepare the polyesterpolyols. The polycarboxylic acids may be aliphatic, cycloaliphatic, araliphatic, aromatic or heterocyclic, and optionally may be substituted, by halogen atoms, for example, and/or unsaturated. Examples thereof that may be mentioned include the following:

oxalic acid, maleic acid, fumaric acid, succinic acid, glutaric acid, adipic acid, sebacic acid, dodecanedioic acid, o-phthalic acid, isophthalic acid, terephthalic acid, trimellitic acid, azelaic acid, 1,4-cyclohexanedicarboxylic acid or tetrahydrophthalic acid, suberic acid, azelaic acid, phthalic anhydride, tetrahydrophthalic anhydride, hexahydrophthalic anhydride, tetrachlorophthalic anhydride, endomethylenetetrahydrophthalic anhydride, glutaric anhydride, maleic anhydride, dimeric fatty acids, their isomers and hydrogenation products, and their esterifiable derivatives, such as anhydrides or dialkyl esters, for example, $C_1$-$C_4$ alkyl esters, preferably methyl, ethyl or n-butyl esters, of the stated acids are employed. Dicarboxylic acids of general formula HOOC—$(CH_2)_y$—COOH are preferred, where y is a number from 1 to 20, preferably an even number from 2 to 20; particular preference is given to succinic acid, adipic acid, sebacic acid, and dodecanedicarboxylic acid.

Suitable polyhydric alcohols for preparing the polyesterols include 1,2-propanediol, ethylene glycol, 2,2-dimethyl-1,2-ethanediol, 1,3-propanediol, 1,2-butanediol, 1,3-butanediol, 1,4-butanediol, 3-methylpentane-1,5-diol, 2-ethylhexane-1, 3-diol, 2,4-diethyloctane-1,3-diol, 1,6-hexanediol, poly-THF with a molar mass between 162 and 2000, poly-1,3-propanediol with a molar mass between 134 and 2000, poly-1,2-propanediol with a molar mass between 134 and 2000, polyethylene glycol with a molar mass between 106 and 2000, neopentylglycol, neopentylglycol hydroxypivalate, 2-ethyl-1,3-propanediol, 2-methyl-1,3-propanediol, 2,2-bis(4-hydroxycyclohexyl)propane, 1,1-, 1,2-, 1,3-, and 1,4-cyclohexanedimethanol, 1,2-, 1,3- or 1,4-cyclohexanediol, trimethylolbutane, trimethylolpropane, trimethylolethane, neopentylglycol, pentaerythritol, glycerol, ditrimethylolpropane, dipentaerythritol, sorbitol, mannitol, diglycerol, threitol, erythritol, adonitol (ribitol), arabitol (lyxitol), xylitol, dulcitol (galactitol), maltitol or isomalt, which if desired may be alkoxylated as described above.

Preference is given to alcohols of the general formula HO—$(CH_2)_x$—OH, where x is a number from 1 to 20, preferably an even number from 2 to 20. Preferred are ethylene glycol, butane-1,4-diol, hexane-1,6-diol, octane-1,8-diol, and dodecane-1,12-diol. Additionally preferred is neopentylglycol.

Also suitable, furthermore, are polycarbonate-diols, of the kind obtainable, for example, by reacting phosgene with an excess of the low molecular weight alcohols stated as synthesis components for the polyesterpolyols.

Lactone-based polyesterdiols are also suitable, these being homopolymers or copolymers of lactones, preferably hydroxyl-terminated adducts of lactones with suitable difunctional starter molecules. Suitable lactones are preferably those deriving from compounds of the general formula HO—$(CH_2)_z$—COOH, where z is a number from 1 to 20, and where one H atom of a methylene unit may also have been substituted by a $C_1$ to $C_4$ alkyl radical. Examples are ε-caprolactone, β-propiolactone, gamma-butyrolactone and/or methyl-ε-caprolactone, 4-hydroxybenzoic acid, 6-hydroxy-2-naphthoic acid or pivalolactone, and mixtures thereof. Examples of suitable starter components are the low molecular weight dihydric alcohols specified above as a synthesis component for the polyesterpolyols. The corresponding polymers of ε-caprolactone are particularly preferred. Lower polyesterdiols or polyetherdiols may also be used as starters for preparing the lactone polymers. Instead of the polymers of lactones it is also possible to use the corresponding, chemically equivalent polycondensates of the hydroxycarboxylic acids corresponding to the lactones.

In the case of the lactone-based polyesterol, preference is given to a polycaprolactone diol, which, formally, is an adduct of caprolactone with a diol HO—R—OH, and which has the formula

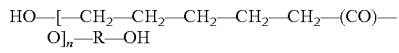

or

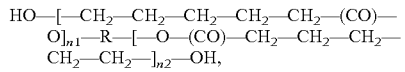

in which n, n1, and n2 are positive integers, for which n=1 to 5 and (n1+n2)=1 to 5, and R is a divalent aliphatic or cycloaliphatic radical having at least one carbon atom, preferably 2 to 20, more preferably 2 to 10, very preferably 3 to 6 carbon atoms.

Aliphatic radicals R are, for example, linear or branched alkylene, e.g., methylene, 1,2-ethylene, 1,2- or 1,3-propylene, 1,2-, 1,3- or 1,4-butylene, 1,1-dimethyl-1,2-ethylene or 1,2-dimethyl-1,2-ethylene, 1,5-pentylene, 1,6-hexylene, 1,8-octylene, 1,10-decylene, or 1,12-dodecylene. Preference is given to 1,2-ethylene, 1,2- or 1,3-propylene, 1,4-butylene and 1,5-pentylene, particular preference to 1,4-butylene, and 1,6-hexylene.

Conceivable, albeit less preferably, are cycloaliphatic radicals, examples being cyclopropylene, cyclopentylene, cyclohexylene, cyclooctylene, and cyclododecylene.

Preferred polyesterols as compounds (a4) have a functionality in terms of free hydroxyl groups of at least 2, more preferably of 2 to 6, very preferably of 2 to 4, more particularly of 2 to 3, and especially of 2 exactly.

The molecular weights $M_n$ of the polyesterols lie preferably between 500 and 4000 ($M_n$ determined by gel permeation chromatography with polystyrene as standard and tetrahydrofuran as eluent).

Component (a5)

Contemplated as component (a5) is at least one, preferably one to three, more preferably one to two, and very preferably precisely one amine of the formula (III)

This component (a5) is reacted at least partly, preferably wholly, with free isocyanate groups, to form urea groups.

The radicals $R^1$ and $R^2$ have been defined above.

Preferred amines (a5) are primary or secondary amines, preferably primary amines, more preferably aniline, substituted anilines in which the phenyl radical carries one or more substituents, benzylamine and benzylamines in which the benzyl radical carries one or more substituents.

Especially preferred are anilines, benzylamines, substituted benzylamines, such as bromo-, chloro-, methoxy-, and fluorobenzylamine, optically active amines as described in WO 2005/005558, especially from page 3 line 19 to page 10, line 4 therein, and also 9-aminofluorene.

Examples of substituted benzylamines are N-methylbenzylamine, N-ethylbenzylamine, N-isopropylbenzylamine, N-phenylbenzylamine, dibenzylamine, 2-methoxybenzylamine, 2-chlorobenzylamine, 4-fluorobenzylamine, 4-methylbenzylamine, 4-methoxybenzylamine, 3-(trifluoromethyl)benzylamine, 2,6-difluorobenzylamine, 3,4-dichlorobenzylamine, N-benzyl-2-phenethylamine, 1-naphthylmethylamine, 4-hydroxy-3-methoxybenzylamine (vanillylamine), 1,2,3,4-tetrahydroisoquinoline, and phenethylamine.

Particularly preferred are aniline and benzylamine, especially benzylamine.

Components (a6)

In the polyurethane(meth)acrylate of the invention it is possible as optional components (a6) to use at least one further compound having precisely one group reactive toward isocyanate groups. That group may be a hydroxyl group, mercapto group, or primary or secondary amino group, but different from component (a5). Suitable compounds (a6) are the customary compounds, known to the skilled worker, which are used typically in polyurethane preparation as what are called stoppers, for lowering the number of reactive free isocyanate groups or for modifying the polyurethane properties. These include, for example, monofunctional alcohols, such as methanol, ethanol, n-propanol, isopropanol, n-butanol etc. Suitable components (a6) are also amines having a primary or secondary amino group, such as methylamine, ethylamine, n-propylamine, diisopropylamine, dimethylamine, diethylamine, di-n-propylamine, diisopropylamine, etc.

Components (a7)

In the polyurethanes of the invention it is possible as optional components (a7) to use at least one diisocyanate or polyisocyanate which is different from the incorporated compounds of components (a1). As components (a7) it is preferred not to use polyisocyanates in which the isocyanate groups have been reacted with a blocking agent.

Preferred compounds (a7) are di- or polyisocyanates having an NCO functionality of 2 to 4.5, more preferably 2 to 3.5. As component (a7) it is preferred to use aliphatic, cycloaliphatic and araliphatic diisocyanates. These may be, for example, the diisocyanates set out above under (a1), but are different from the compound (a1) actually used in the polyurethane. Preferred compounds (a7) are those which in addition to 2 or more isocyanate groups also contain a group selected from the group of urethane, urea, biuret, allophanate, carbodiimide, urethonimine, uretdione, and isocyanurate groups.

These are, for example, the polyisocyanate described above under (a1), as identified with the numbers 1) to 10), or mixtures thereof.

As component (a7) it is preferred to use 1,6-hexamethylene diisocyanate, isophorone diisocyanate, 1,3- and 1,4-bis(isocyanatomethyl)cyclohexane, their Isocyanurates, biurets, and mixtures thereof.

Where the polyurethane acrylates of the invention comprise, as well as component (a1), a component (a7), the fraction of the compounds of component (a7) is preferably 0.1% to 90%, more preferably 1% to 50%, more particularly 5% to 30%, by weight, based on the total amount of the compounds of components (a1) and (a7).

In one preferred embodiment, apart from components (a1), no further component (a7) is incorporated into the polyurethane(meth)acrylates (A).

Component (C)

The mixture of polyurethanes (A) according to the invention may optionally comprise at least one further compound (C) such as is normally employed as a reactive diluent. These include, for example, the reactive diluents as described in P. K. T. Oldring (editor), Chemistry & Technology of UV & EB Formulations for Coatings, Inks & Paints, Vol. II, Chapter III: Reactive Diluents for UV & EB Curable Formulations, Wiley and SITA Technology, London 1997.

Preferred reactive diluents are compounds different from component (a2) which have at least one free-radically polymerizable C=C double bond.

Examples of reactive diluents include esters of (meth) acrylic acid with alcohols which have 1 to 20 C atoms, e.g., methyl(meth)acrylate, ethyl(meth)acrylate, n-butyl(meth) acrylate, tert-butyl(meth)acrylate, 2-ethylhexyl(meth)acrylate, dihydrodicyclopentadienyl acrylate, vinylaromatic compounds, e.g., styrene, divinylbenzene, α,β-unsaturated nitriles, e.g., acrylonitrile, methacrylonitrile, α,β-unsaturated aldehydes, e.g., acrolein, methacrolein, vinyl esters, e.g., vinyl acetate, vinyl propionate, halogenated ethylenically unsaturated compounds, e.g., vinyl chloride, vinylidene chloride, conjugated unsaturated compounds, e.g., butadiene, isoprene, chloroprene, monounsaturated compounds, e.g., ethylene, propylene, 1-butene, 2-butene, isobutene, cyclic monounsaturated compounds, e.g., cyclopentene, cyclohexene, cyclododecene, N-vinylformamide, allylacetic acid, vinylacetic acid, monoethylenically unsaturated carboxylic acids having 3 to 8 C atoms and also their water-soluble alkali metal, alkaline earth metal or ammonium salts, such as, for example: acrylic acid, methacrylic acid, dimethylacrylic acid, ethacrylic acid, maleic acid, citraconic acid, methylenemalonic acid, crotonic acid, fumaric acid, mesaconic acid, and itaconic acid, maleic acid, N-vinylpyrrolidone, N-vinyl lactams, such as N-vinylcaprolactam, N-vinyl-N-alkylcarboxamides or N-vinylcarboxamides, such as N-vinylacetamide, N-vinyl-N-methylformamide, and N-vinyl-N-methylacetamide or vinyl ethers, e.g., methyl vinyl ether, ethyl vinyl ether, n-propyl vinyl ether, isopropyl vinyl ether, n-butyl vinyl ether, sec-butyl vinyl ether, isobutyl vinyl ether, tert-butyl vinyl ether, 4-hydroxybutyl vinyl ether, and mixtures thereof.

Further suitable reactive diluents are trimethylolpropane monoformal acrylate, glycerol formal acrylate, 4-tetrahydropyranyl acrylate, 2-tetrahydropyranyl methacrylate, and tetrahydrofurfuryl acrylate.

Compounds having at least two free-radically polymerizable C=C double bonds: these include, in particular, the diesters and polyesters of the aforementioned α,β-ethylenically unsaturated monocarboxylic and/or dicarboxylic acids with diols or polyols. Particularly preferred are hexanediol diacrylate, hexanediol dimethacrylate, octanediol diacrylate, octanediol dimethacrylate, nonanediol diacrylate, nonanediol dimethacrylate, decanediol diacrylate, decanediol dimethacrylate, pentaerythritol diacrylate, dipentaerythritol tetraacrylate, dipentaerythritol triacrylate, pentaerythritol tetraacrylate, etc. Also preferred are the esters of alkoxylated polyols, with α,β-ethylenically unsaturated monocarboxylic and/or dicarboxylic acids, such as the polyacrylates or polymethacrylates which on average per OH group are singly to decuply, preferably singly to pentuply, more preferably singly to triply, and very preferably singly to doubly alkoxylated, for example ethoxylated and/or propoxylated, preferably ethoxlyated or propoxylated, and more preferably exclusively ethoxylated trimethylolpropane, glycerol or pentaerythritol. Additionally suitable are the esters of alicyclic diols, such as cyclohexanediol di(meth)acrylate and bis(hydroxymethylethyl)cyclohexane di(meth)acrylate.

Further suitable reactive diluents are for example urethane (meth)acrylates, epoxy(meth)acrylates, polyether(meth) acrylates, polyester(meth)acrylates or polycarbonate(meth) acrylates.

Urethane(meth)acrylates

Urethane(meth)acrylates are obtainable for example by reacting polyisocyanates with hydroxyalkyl(meth)acrylates or hydroxyalkyl vinyl ethers and, optionally chain extenders such as diols, polyols, diamines, polyamines, dithiols or polythiols.

Urethane(meth)acrylates of this kind comprise as synthesis components substantially:

(1) at least one organic aliphatic, aromatic or cycloaliphatic di- or polyisocyanate, such as those listed above under (a1), for example
(2) at least one compound having at least one isocyanate-reactive group and at least one free-radically polymerizable unsaturated group, such as those listed under (a2), for example, and
(3) optionally, at least one compound having at least two isocyanate-reactive groups, such as those listed under (a3), for example.

Components (1), (2), and (3) may be the same as those described above for the polyurethanes (A) of the invention.

The urethane(meth)acrylates preferably have a number-average molar weight $M_n$ of 500 to 20 000, in particular of 500 to 10 000 and more preferably 600 to 3000 g/mol (determined by gel permeation chromatography using tetrahydrofuran and polystyrene as standard).

The urethane(meth)acrylates preferably have a (meth) acrylic group content of 1 to 5, more preferably of 2 to 4, mol per 1000 g of urethane(meth)acrylate.

Particularly preferred urethane(meth)acrylates have an average OH functionality of 1.5 to 4.5.

Epoxy(meth)acrylates

Epoxy(meth)acrylates are preferably obtainable by reacting epoxides with (meth)acrylic acid. Examples of suitable epoxides include epoxidized olefins, aromatic glycidyl ethers or aliphatic glycidyl ethers, preferably those of aromatic or aliphatic glycidyl ethers.

Examples of possible epoxidized olefins include ethylene oxide, propylene oxide, isobutylene oxide, 1-butene oxide, 2-butene oxide, vinyloxirane, styrene oxide or epichlorohydrin, preference being given to ethylene oxide, propylene oxide, isobutylene oxide, vinyloxirane, styrene oxide or epichlorohydrin, particular preference to ethylene oxide, propylene oxide or epichlorohydrin, and very particular preference to ethylene oxide and epichlorohydrin.

Aromatic glycidyl ethers are, for example, bisphenol A diglycidyl ether, bisphenol F diglycidyl ether, bisphenol B diglycidyl ether, bisphenol S diglycidyl ether, hydroquinone diglycidyl ether, alkylation products of phenol/dicyclopentadiene, e.g., 2,5-bis[(2,3-epoxy-propoxy)phenyl]octahydro-4,7-methano-5H-indene) (CAS No. [13446-85-0]), tris[4-(2,3-epoxypropoxy)phenyl]methane isomers (CAS No. [66072-39-7]), phenol-based epoxy novolaks (CAS No. [9003-35-4]), and cresol-based epoxy novolaks (CAS No. [37382-79-9]).

Preference is given to bisphenol A diglycidyl ether, bisphenol F diglycidyl ether, bisphenol B diglycidyl ether, and bisphenol S diglycidyl ether, and bisphenol A diglycidyl ether is particularly preferred.

Examples of aliphatic glycidyl ethers include 1,4-butanediol diglycidyl ether, 1,6-hexanediol diglycidyl ether, trimethylolpropane triglycidyl ether, pentaerythritol tetraglycidyl ether, 1,1,2,2-tetrakis[4-(2,3-epoxypropoxy)phenyl]ethane (CAS No. [27043-37-4]), diglycidyl ether of polypropylene glycol (α,ω-bis(2,3-epoxypropoxy)poly(oxypropylene) (CAS No. [16096-30-3]) and of hydrogenated bisphenol A (2,2-bis[4-(2,3-epoxypropoxy)cyclohexyl]propane, CAS No. [13410-58-7]).

Preference is given to 1,4-butanediol diglycidyl ether, 1,6-hexanediol diglycidyl ether, trimethylolpropane triglycidyl ether, pentaerythritol tetraglycidyl ether, and 2,2-bis[4-(2,3-epoxypropoxy)cyclohexyl]propane.

The abovementioned aromatic glycidyl ethers are particularly preferred.

The epoxy(meth)acrylates and epoxy vinyl ethers preferably have a number-average molar weight $M_n$ of 200 to 20 000, more preferably of 200 to 10 000 g/mol, and very preferably of 250 to 3000 g/mol; the amount of (meth)acrylic or vinyl ether groups is preferably 1 to 5, more preferably 2 to 4, per 1000 g of epoxy(meth)acrylate or vinyl ether epoxide (determined by gel permeation chromatography using polystyrene as standard and tetrahydrofuran as eluent).

Preferred epoxy(meth)acrylates have an OH number of 40 to 400 mg KOH/g.

Preferred epoxy(meth)acrylates have an average OH functionality of 1.5 to 4.5.

Particularly preferred epoxy(meth)acrylates are those such as are obtained from processes in accordance with EP-A-54 105, DE-A 33 16 593, EP-A 680 985, and EP-A-279 303, in which in a first stage a (meth)acrylic ester is prepared from (meth)acrylic acid and hydroxy compounds and in a second stage excess (meth)acrylic acid is reacted with epoxides.

Polyester(meth)acrylates

Suitable polyester(meth)acrylates are at least partly or, preferably, completely (meth)acrylated reaction products of polyesterols of the kind listed above under compounds (a4).

Carbonate(meth)acrylates

Carbonate(meth)acrylates comprise on average preferably 1 to 5, especially 2 to 4, more preferably 2 to 3 (meth)acrylic groups, and very preferably 2 (meth)acrylic groups.

The number-average molecular weight $M_n$ of the carbonate (meth)acrylates is preferably less than 3000 g/mol, more preferably less than 1500 g/mol, very preferably less than 800 g/mol (determined by gel permeation chromatography using polystyrene as standard, tetrahydrofuran as solvent).

The carbonate(meth)acrylates are obtainable in a simple manner by transesterifying carbonic esters with polyhydric, preferably dihydric, alcohols (diols, hexanediol for example) and subsequently esterifying the free OH groups with (meth) acrylic acid, or else by transesterification with (meth)acrylic esters, as described for example in EP-A 92 269. They are also obtainable by reacting phosgene, urea derivatives with polyhydric, e.g., dihydric, alcohols.

In an analogous way it is also possible to obtain vinyl ether carbonates, by reacting a hydroxyalkyl vinyl ether with carbonic esters and also, optionally, with dihydric alcohols.

Also conceivable are (meth)acrylates or vinyl ethers of polycarbonate polyols, such as the reaction product of one of the aforementioned diols or polyols and a carbonic ester and also a hydroxyl-containing (meth)acrylate or vinyl ether.

Examples of suitable carbonic esters include ethylene carbonate, 1,2- or 1,3-propylene carbonate, dimethyl carbonate, diethyl carbonate or dibutyl carbonate.

Examples of suitable hydroxyl-containing (meth)acrylates are 2-hydroxyethyl(meth)acrylate, 2- or 3-hydroxypropyl (meth)acrylate, 1,4-butanediol mono(meth)acrylate, neopentylglycol mono(meth)acrylate, glyceryl mono- and di(meth) acrylate, trimethylolpropane mono- and di(meth)acrylate, and pentaerythrityl mono-, di-, and tri(meth)acrylate.

Suitable hydroxyl-containing vinyl ethers are, for example, 2-hydroxyethyl vinyl ether and 4-hydroxybutyl vinyl ether.

Particularly preferred carbonate(meth)acrylates are those of the formula:

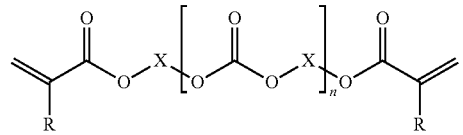

in which R is H or $CH_3$, X is a $C_2$-$C_{18}$ alkylene group, and n is an integer from 1 to 5, preferably 1 to 3.

R is preferably H and X is preferably $C_2$ to $C_{10}$ alkylene, examples being 1,2-ethylene, 1,2-propylene, 1,3-propylene, 1,4-butylene, and 1,6-hexylene, more preferably $C_4$ to $C_8$ alkylene. With very particular preference X is $C_6$ alkylene.

The carbonate(meth)acrylates are preferably aliphatic carbonate(meth)acrylates.

They further include customary polycarbonates known to the skilled worker and having terminal hydroxyl groups, which are obtainable, for example, by reacting the aforementioned diols with phosgene or carbonic diesters.

Polyether(meth)acrylates

Polyether(meth)acrylates are preferably (meth)acrylates of singly to vigintuply and more preferably triply to decuply ethoxylated, propoxylated or mixedly ethoxylated and propoxylated, and more particularly exclusively ethoxylated, neopentylglycol, trimethylolpropane, trimethylolethane or pentaerythritol.

In addition it is possible to use singly to vigintuply and more preferably triply to decuply ethoxylated, propoxylated or mixedly ethoxylated and propoxylated, and more particularly exclusively ethoxylated, glycerol.

Preferred polyfunctional, polymerizable compounds are ethylene glycol diacrylate, 1,2-propanediol diacrylate, 1,3-propanediol diacrylate, 1,4-butanediol diacrylate, 1,6-hexanediol diacrylate, trimethylolpropane triacrylate, pentaerythrityl tetraacrylate, polyesterpolyol acrylates, polyetherol acrylates, and triacrylate of singly to vigintuply alkoxylated, more preferably ethoxylated, trimethylolpropane.

Polyether(meth)acrylates may further be (meth)acrylates of polyTHF having a molar weight between 162 and 2000, poly-1,3-propanediol having a molar weight between 134 and 2000, or polyethylene glycol having a molar weight between 238 and 2000.

Where the coating composition or polyurethane acrylates of the invention are cured not with electron beams but instead by means of UV radiation, the preparations of the invention preferably comprise at least one photoinitiator (B) which is able to initiate the polymerization of ethylenically unsaturated double bonds.

Photoinitiators may be, for example, photoinitiators known to the skilled worker, examples being those specified in "Advances in Polymer Science", Volume 14, Springer Berlin 1974 or in K. K. Dietliker, Chemistry and Technology of UV and EB Formulation for Coatings, Inks and Paints, Volume 3; Photoinitiators for Free Radical and Cationic Polymerization, P. K. T. Oldring (Eds), SITA Technology Ltd, London.

Suitability is possessed by those photoinitiators (B) as described in WO 2006/005491 A1, page 21 line 18 to page 22 line 2 (corresponding to US 2006/0009589 A1, paragraph [0150]), which is hereby considered part of the present disclosure through reference.

Also suitable are nonyellowing or low-yellowing photoinitiators of the phenylglyoxalic ester type, as described in DE-A 198 26 712, DE-A 199 13 353 or WO 98/33761.

Typical mixtures comprise, for example, 2-hydroxy-2-methyl-1-phenylpropan-2-one and 1-hydroxycyclohexyl phenyl ketone, bis(2,6-dimethoxybenzoyl)-2,4,4-trimethylpentylphosphine oxide and 2-hydroxy-2-methyl-1-phenylpropan-1-one, benzophenone and 1-hydroxycyclohexyl phenyl ketone, bis(2,6-dimethoxybenzoyl)-2,4,4-trimethylpentylphosphine oxide and 1-hydroxycyclohexyl phenyl ketone, 2,4,6-trimethylbenzoyldiphenylphosphine oxide and 2-hydroxy-2-methyl-1-phenylpropan-1-one, 2,4,6-trimethylbenzophenone and 4-methylbenzophenone or 2,4,6-trimethylbenzophenone, and 4-methylbenzophenone and 2,4,6-trimethylbenzoyldiphenylphosphine oxide.

Preference among these photoinitiators is given to 2,4,6-trimethylbenzoyldiphenylphosphine oxide, ethyl 2,4,6-trimethylbenzoylphenylphosphinate, bis(2,4,6-tri-methylbenzoyl)phenylphosphine oxide, benzophenone, 1-hydroxycycohexyl phenyl ketone, 1-benzoylcyclohexan-1-ol, 2-hydroxy-2,2-dimethylacetophenone, 2,2-dimethoxy-2-phenylacetophenone, and mixtures thereof.

The coating compositions of the invention comprise the photoinitiators preferably in an amount of 0.05% to 10%, more preferably 0.1% to 8%, in particular 0.2% to 5%, by weight based on the total amount of polyurethanes (A).

The rheology of a coating composition can be adjusted by preparing the rheological assistant (A) of the invention, as described above, in a solvent and then mixing this solution of the rheological assistant (A), prior to application, with component (C) and also, optionally, further customary coatings additives to form the coating composition.

Preference, however, is given to the embodiment of preparing the rheological assistant (A) in a reactive diluent, preferably in at least part, and more preferably in the entirety, of component (C) and so producing the coating composition in ready-to-apply form, without the need for a solvent, optionally with further admixing of customary coatings additives.

In one preferred embodiment of the present invention, the amount of urea groups of the formula (I) in the coating compositions, based on the sum of components (A) and (C), is at least 0.03 mol of urea groups of the formula (I) per kg of the sum of components (A) and (C), more preferably at least 0.05 mol/kg, very preferably at least 0.07 mol/kg.

Generally speaking, the amount of urea groups of the formula (I) ought not to exceed a level of 0.5 mol/kg, preferably not more than 0.3 mol/kg, more preferably not more than 0.2 mol/kg, and very preferably not more than 0.1 mol/kg.

The coating compositions of the invention may optionally comprise further customary coatings additives, such as flow control agents, defoamers, UV absorbers, sterically hindered amines (HALS), plasticizers, antisettling agents, dyes, pigments, antioxidants, activators (accelerants), antistatic agents, flame retardants, surface-active agents, viscosity modifiers other than those described in this specification, plastifying agents or chelating agents and/or fillers.

The polyurethanes (A) of the invention may comprise 0% to 10% by weight, based on the sum of the compounds (A), of at least one UV stabilizer.

Suitable stabilizers comprise typical UV absorbers such as oxanilides, triazines, preferably hydroxyphenyltriazine, and benzotriazole (the latter obtainable as Tinuvin® grades from Ciba Spezialitatenchemie or BASF), and benzophenones.

These stabilizers can be used alone or together with, based on the sum of the compounds (A), additionally 0% to 5% by weight of suitable free-radical scavengers, examples being sterically hindered amines such as 2,2,6,6-tetramethylpiperidine, 2,6-di-tert-butylpiperidine or derivatives thereof, e.g., bis(2,2,6,6-tetramethyl-4-piperidyl) sebacinate or, preferably, bis(1,2,2,6,6-pentamethyl-4-piperidyl) sebacate.

Additionally it is possible for one or more thermally activable initiators to be added, examples being potassium peroxodisulfate, dibenzoyl peroxide, cyclohexanone peroxide, di-tert-butyl peroxide, azobisisobutyronitrile, cyclohexylsulfonyl acetyl peroxide, diisopropyl percarbonate, tert-butyl peroctoate or benzpinacol, and also, for example, those thermally activable initiators which have a half-life at 80° C. of more than 100 hours, such as di-tert-butyl peroxide, cumene hydroperoxide, dicumyl peroxide, tert-butyl perbenzoate, silylated pinacols, which are available commercially, for example, under the trade name ADDID 600 from Wacker, or amine N-oxides containing hydroxyl groups, such as 2,2,6,6-tetramethylpiperidine-N-oxyl, 4-hydroxy-2,2,6,6-tetramethylpiperidine-N-oxyl, etc.

Further examples of suitable initiators are described in "Polymer Handbook", 2nd ed., Wiley & Sons, New York.

Examples of chelating agents which can be used include ethylenediamineacetic acid and salts thereof, and also β-diketones.

Suitable fillers comprise silicates, e.g., silicates obtainable by hydrolysis of silicon tetrachloride, such as Aerosil R from Degussa, siliceous earth, talc, aluminum silicates, magnesium silicates, and calcium carbonates, etc. Suitable stabilizers comprise typical UV absorbers such as oxanilides, triazines, and benzotriazole (the latter obtainable as Tinuvin R grades from Ciba Spezialitätenchemie or BASF), and benzophenones. They can be used alone or together with suitable free-radical scavengers, examples being sterically hindered amines such as 2,2,6,6-tetramethylpiperidine, 2,6-di-tert-butylpiperidine or derivatives thereof, e.g., bis(2,2,6,6-tetramethyl-4-piperidyl) sebacate. Stabilizers are used usually in amounts of 0.1% to 5.0% by weight, based on the "solid" components comprised in the preparation.

The polyurethanes (A) of the invention are used preferably as mixtures with the reactive diluents (C).

In this context, the fraction of the polyurethanes (A) as a proportion of the total amount of (A) and (C) is generally from 1% by weight to 30% by weight, preferably from 2% to 25% by weight, more preferably from 5% to 20% by weight, very preferably from 7% to 15% by weight, and more particularly from 10% to 15% by weight.

The composition of the polyurethanes (A) of the invention per 100 mol % of reactive isocyanate groups in (a1) and (a7) (in total) is generally as follows:
- (a2) 30 to 95 mol %, preferably 40 to 92 mol %, more preferably 50 to 90 mol %, very preferably 60 to 80 mol %, and in particular 70 to 80 mol %,
- (a3) 0 to 30 mol %, preferably 0 to 25 mol %, more preferably 0 to 20 mol %, very preferably 0 to 15 mol %, in particular 0 to 10 mol %, and specifically 0 mol %,
- (a4) 0 to 10 mol %, preferably 0 to 8 mol %, more preferably 0 to 5 mol %, very preferably 0 to 3 mol %, and in particular 0 mol %,
- (a5) 5 up to 30 mol %, preferably 8 to 25 mol %, more preferably 10 to 20 mol %, very preferably 15 to 20 mol %, and in particular 18 to 20 mol %,
- (a6) up to 10 mol %, preferably up to 8 mol %, more preferably up to 5 mol %, very preferably up to 2 mol %, and in particular 0 mol %, based in each case on the isocyanate-reactive groups, with the proviso that the sum of all the isocyanate-reactive groups is 80 to 125 mol % of the reactive isocyanate groups in (a1) and (a7) (in total), preferably 85 to 115 mol %, more preferably 90 to 110 mol %, very preferably 95 to 105 mol %, and in particular 100 mol %.

The ratio of (a1) to (a7), based on the reactive isocyanate groups, is generally 1:0 to 1:2, preferably 1:0 to 1:1.5, more preferably 1:0 to 1:1.2, very preferably 1:0 to 1:1, in particular 1:0 to 1:0.5, and especially 1:0.

The number-average molecular weight $M_n$ of the polyurethanes (A) of the invention, determined by gel permeation chromatography using tetrahydrofuran as eluent and polystyrene as standard, can amount for example to up to 50 000, preferably up to 30 000, more preferably up to 10 000, and in particular up to 5000.

The isocyanate group content, calculated as NCO with the molecular weight 42 g/mol, is up to 5% by weight in the polyurethanes of the invention, preferably up to 3% by weight, more preferably up to 2% by weight, very preferably up to 1% by weight, and in particular up to 0.5% by weight. In one specific embodiment the free isocyanate group content of (A) is 0% by weight. If blocked isocyanate groups are comprised then they are included in the calculation of the isocyanate group content.

The polyurethane (A) preferably has a glass transition temperature of more than 20° C., preferably more than 25° C.

The glass transition temperature Tg is determined by the DSC method (Differential Scanning Calorimetry) according to ASTM 3418/82 at a heating rate of 10° C./min.

For the preparation of the polyurethanes of the invention the starting components (a1) to (a7), if used, are reacted with one another at temperatures of 40 to 180° C., preferably 50 to 150° C., while observing the NCO/OH equivalent ratio specified above.

The reaction generally takes place until the desired NCO number to DIN 53185 has been reached.

The reaction time is generally 10 minutes to 12 hours, preferably 15 minutes to 10 hours, more preferably 20 minutes to 8 hours, and very preferably 1 to 8 hours.

The reaction can optionally be accelerated using suitable catalysts.

The formation of the adduct of isocyanato-functional compound and the compound comprising groups that are reactive toward isocyanate groups takes place generally by mixing the components in any order, at elevated temperature optionally.

Preferably the compound comprising groups that are reactive toward isocyanate groups is added to the isocyanato-functional compound, more preferably in two or more steps.

With particular preference the isocyanato-functional compound is introduced initially and the compounds comprising isocyanate-reactive groups are added. In particular the isocyanato-functional compound (a1) is introduced first of all, followed by (a2) and then (a5) is added, or, preferably, the isocyanato-functional compound (a1) is introduced first of all, and then (a5) and subsequently (a2) is added. After that it is possible optionally to add further desired components.

It will be appreciated that (a2) and (a5) can also be added in a mixture with one another.

For the preparation of the coating compositions the polyurethane prepared can be mixed with the reactive diluent (C); in one preferred embodiment, the polyurethane acrylate (A) is prepared in at least a portion of the reactive diluent (C).

The coating compositions of the invention are particularly suitable for coating substrates such as wood, paper, textile, leather, nonwoven, plastics surfaces, glass, ceramic, mineral building materials, such as cement moldings and fiber-cement slabs, and, in particular, for coating metals or coated metals.

After curing by means of high-energy radiation, the coating compositions of the invention advantageously form films having good performance properties, such as good scratch resistance, good chemical resistance, good weathering stability and/or good mechanical properties.

The substrates are coated in accordance with customary methods that are known to the skilled worker, involving the application of at least one coating composition of the invention to the substrate that is to be coated, in the desired thickness. This process can be repeated one or more times if desired. Application to the substrate may take place in a known way, e.g., by spraying, troweling, knifecoating, brushing, rolling, roller-coating or pouring. The coating thickness is generally situated within a range from about 3 to 1000 g/m² and preferably 10 to 200 g/m².

To remove volatiles, e.g., solvent, the coating can be dried following application to the substrate, drying taking place for example in a tunnel oven or by flashing off. Drying can also take place by means of NIR radiation, NIR radiation here meaning electromagnetic radiation in the wavelength range from 760 nm to 2.5 µm, preferably from 900 to 1500 nm.

Optionally, if two or more films of the coating material are applied one on top of another, a radiation cure may take place after each coating operation.

Radiation curing is accomplished by exposure to high-energy radiation, i.e., UV radiation or daylight, preferably light with a wavelength of 250 to 600 nm, or by irradiation with high-energy electrons (electron beams; 150 to 300 keV). Examples of radiation sources used include high-pressure mercury vapor lamps, lasers, pulsed lamps (flash light), halogen lamps or excimer emitters. The radiation dose normally sufficient for crosslinking in the case of UV curing is situated within the range from 80 to 3000 mJ/cm².

Irradiation may also optionally be carried out in the absence of oxygen, e.g., under an inert gas atmosphere. Suitable inert gases include, preferably, nitrogen, noble gases, carbon dioxide or combustion gases. Irradiation may also take place with the coating composition being covered by transparent media. Transparent media are, for example, polymeric films, glass or liquids, e.g., water. Particular preference is given to irradiation in the manner as is described in DE-A1199 57 900.

In one preferred process, curing takes place continuously, by passing the substrate treated with the preparation of the invention at constant speed past a radiation source. For this it is necessary for the cure rate of the preparation of the invention to be sufficiently high.

This varied course of curing over time can be exploited in particular when the coating of the article is followed by a further processing step in which the film surface comes into direct contact with another article or is worked on mechanically.

The invention further provides for the use of a coating composition, as described above, for coating substrates of metal, wood, paper, ceramic, glass, plastic, textile, leather, nonwoven, or mineral building materials.

The coating compositions of the invention can be used in particular as primers, primer-surfacers, pigmented topcoat materials, and clearcoat materials in the sectors of industrial coating, especially aircraft coating or large-vehicle coating, wood coating, automotive finishing, especially OEM finishing or automotive refinish, or decorative coating. The coating materials are especially suitable for applications where particularly high application reliability, exterior weathering stability, optical qualities, solvent resistance and/or chemical resistance, and also scratch resistance are required.

The invention further provides for the use of the polyurethanes (A) as viscosity regulators, preferably as viscosity regulators for radiation-curable coating compositions.

The invention is illustrated by means of the following, nonlimiting examples.

EXAMPLES

Unless indicated otherwise, parts and percentages indicated are by weight.

The following compounds were used in the examples:

Laromer® LR 8863 from BASF, Ludwigshafen: triacrylate of trimethylolpropane with on average approximately 3.5-fold ethoxylation.

Laromer® LR9000 from BASF, Ludwigshafen: isocyanato acrylate containing allophanate groups and based on 1,6-hexamethylene diisocyanate, having an NCO value of 14.5%-15.5%, a viscosity to DIN EN ISO 3219 (shear rate D) at 23° C. of 1000 to 1400 mPas, and a double bond density of approximately 3.5 mol/kg.

Laromer® LR 8987 from BASF, Ludwigshafen: polyurethane acrylate containing isocyanurate groups and biuret groups and based on 1,6-hexamethylene diisocyanate, as 70% strength solution in 1,6-hexanediol diacrylate, double bond density of approximately 5 mol/kg, viscosity to DIN EN ISO 3219 (shear rate D, 100 s$^{-1}$) at 23° C. of 4 to 6 Pas.

Laromer® UA 9050 from BASF, Ludwigshafen: polyurethane acrylate isocyanato acrylate containing allophanate groups and based on 1,6-hexamethylene diisocyanate, having a double bond density of approximately 7 mol/kg.

Basonat® HI100 from BASF, Ludwigshafen: polyisocyanurate based on 1,6-hexamethylene diisocyanate, NCO value 21.5%-22.5%, viscosity to DIN EN ISO 3219 (shear rate D) at 23° C. 2500-4000 mPas Irgacure® 184 1-hydroxycyclohexyl phenyl ketone Lucirin® TPO 2,4,6-trimethylbenzoyldiphenylphosphine oxide Irgacure® 500 1:1 mixture of 50% by weight of 1-hydroxycyclohexyl phenyl ketone and 50% by weight of benzophenone

Example 1

900 parts of a polyether acrylate (Laromer® LR 8863) and 34.5 parts of an isocyanato acrylate (Laromer® LR9000) were charged to a reaction flask and 13.2 parts of benzylamine were added dropwise at room temperature over the course of 5 minutes with vigorous stirring (3000 rpm), during which the temperature rose slightly. Stirring was then continued at 2500 rpm for a further 30 minutes. The reaction mixture became cloudy and, after approximately 15 minutes, gelatinous. After cooling, the reaction mixture no longer flowed, but could be brought back to the liquid state by shearing or shaking.

Example 2

300 parts of a polyurethane acrylate (Laromer® LR 8987) and 2.87 parts of an isocyanato acrylate (Laromer® LR9000) were charged to a reaction flask and 1.1 parts of benzylamine were added dropwise at room temperature over the course of 5 minutes with vigorous stirring (3000 rpm), during which the temperature rose slightly. Stirring was then continued at 4000 rpm for 30 minutes more. The reaction mixture became highly viscous. The reaction mixture became lower in viscosity by shearing or shaking.

Example 3

300 parts of a polyurethane acrylate (Laromer® LR 8987) and 11.5 parts of an isocyanato acrylate (Laromer® LR9000) were charged to a reaction flask and 4.4 parts of benzylamine were added dropwise at room temperature over the course of 5 minutes with vigorous stirring (3000 rpm), during which the temperature rose slightly. Stirring was then continued at 4000 rpm for a further 30 minutes. The reaction mixture became of very high viscosity. After cooling, the reaction mixture no longer flowed, but could be brought back to the liquid state by shearing or shaking.

Example 4

25 parts of example 3 were added to 175 parts of a polyurethane acrylate (Laromer® LR 8987) and the mixture was homogenized at 80° C. using a dissolver at 4000 rpm (dispersing disk 3 cm) for 2 hours.

The mixture was homogeneous and had a higher viscosity than the polyurethane acrylate alone (Laromer® LR 8987).

Example 5

100 parts of a polyisocyanurate (Basonat® HI100) and 20.25 parts of hydroxyethyl acrylate were mixed at room temperature, admixed with 0.03 part of dibutyltin dilaurate, and stirred at 60° C. for 3 hours. The NCO value dropped from 22% to 12.2%. 3.6 parts of the isocyanato acrylate thus prepared were introduced into a feed vessel. In the reservoir flask, 90 parts of a polyether acrylate (Laromer® LR 8863) were introduced, and this reservoir was added slowly dropwise with vigorous stirring. It was then admixed, with vigorous stirring (2500 rpm), with 1.1 parts of benzylamine. When the slightly exothermic reaction had subsided, stirring was continued for 30 minutes more. The reaction mixture became cloudy and gelled after about 15 minutes. However, it could be brought back to the liquid state by shearing or shaking.

Example 6

64 parts of a polyurethane acrylate (Laromer® UA 9050), 50 parts of an isocyanato acrylate (Laromer® LR9000), 75 parts of a monoacrylate (tert-butylcyclohexyl acrylate), 2.4 parts of Tinuvin® 400 (2-[4-[2-hydroxy-3-tridecyloxypropyl]oxy]-2-hydroxyphenyl]-4,6-bis(2,4-dimethylphenyl)-1,3,5-triazine and 2-[4-[2-hydroxy-3-didecyloxypropyl]oxy]-2-hydroxyphenyl]-4,6-bis(2,4-dimethylphenyl)-1,3,5-triazine), 1.2 parts of Tinuvin® 292 (bis(1,2,2,6,6-pentamethyl-4-piperidyl)sebacate), and 5 parts of a photoinitiator mixture (Irgacure® 184 and Lucirin® TPO 8:2) were charged to a reaction flask and 3.4 parts of benzylamine were added dropwise at room temperature over the course of 5 minutes with vigorous stirring (3000 rpm), during which the temperature rose slightly. Stirring was then continued at 4000 rpm for 30 minutes more. The reaction mixture became of very high viscosity.

Example 7

900 parts of a polyether acrylate (Laromer® LR 8863) and 34.5 parts of an isocyanato acrylate (Laromer® LR9000) were charged to a reaction flask and 13.2 parts of benzylamine were added dropwise at room temperature over the course of 5 minutes with vigorous stirring (3000 rpm), during which the temperature rose slightly. Stirring was then continued at 2500 rpm for a further 30 minutes. The reaction mixture became cloudy and, after approximately 15 minutes, gelatinous. After cooling, the reaction mixture no longer flowed, but could be brought back to the liquid state by shearing or shaking.

Example 8

Comparison of Film Properties 10 parts each of the unadditized Laromer® 8863 and of the reaction products from example 1 and example 7 were admixed each with 0.2 part of the photoinitiator Irgacure® 500, and the formulation was drawn down on to glass using a four-way bar applicator with a 100 µm slot, and the drawdowns were exposed in air under a UV lamp with 1400 mJ/cm².

The resulting pendulum damping values are as follows:

| Reference Laromer ® 8863 | 115 s |
|---|---|
| Example 1: | 113 s |
| Example 7: | 108 s |

Example 9

100 parts of a polyether acrylate (Laromer® LR 8863) and 4.5 parts of a reaction product of 2.25 parts of the isocyanato acrylate (Laromer® LR9000) with one part of a polyester formed from adipic acid and neopentyl glycol, with a molecular weight of approximately 500 g/mol (OH number 224), were charged to a reaction flask and 0.65 part of benzylamine were added dropwise at room temperature over the course of 5 minutes with vigorous stirring (3000 rpm), during which the temperature rose slightly. Stirring was then continued at 2500 rpm for a further 30 minutes. The reaction mixture became cloudy and, after approximately 3 hours, gelatinous. After cooling, the reaction mixture no longer flowed, but could be brought back to the liquid state by shearing or shaking.

Example 10

100 parts of a polyether acrylate (Laromer® LR 8863) and 7.04 parts of a reaction product of 1.12 parts of the isocyanato acrylate (Laromer® LR9000) with one part of a polyester formed from adipic acid and butanediol, with a molecular weight of approximately 1000 g/mol (OH number 112), were charged to a reaction flask and 0.66 part of benzylamine were added dropwise at room temperature over the course of 5 minutes with vigorous stirring (3000 rpm), during which the temperature rose slightly. Stirring was then continued at 2500 rpm for a further 30 minutes. The reaction mixture became cloudy and, after approximately 3 hours, gelatinous. After cooling, the reaction mixture no longer flowed, but could be brought back to the liquid state by shearing or shaking.

The invention claimed is:

1. A rheological assistant comprising
at least one (meth)acrylate group and connected thereto
at least one urea group of the formula (I)

$$-NH-(CO)-NR^1R^2 \qquad (I)$$

in which
$R^1$ and $R^2$ each independently of one another are hydrogen, alkyl, aryl, cycloalkyl or aralkyl, with the proviso that at least one of the radicals is other than hydrogen, which rheological assistant is synthesized from (a1) at least one polyisocyanate based on aliphatic and/or cycloaliphatic diisocyanates, the polyisocyanate comprising an isocyanato acrylate containing allophanate group, (a2) at least one compound having at least one group reactive toward isocyanate groups, and at least one free-radically polymerizable C=C double bond, wherein the at least one compound having at least one group reactive toward isocyanate groups reacts with the at least one polyisocyanate such that the at least one group having at least one group reactive toward isocyanate groups is attached via the isocyanato acrylate containing allophanate group of the at least one polyisocyanate, (a3) optionally at least one compound having at least two groups reactive toward isocyanate groups and selected from hydroxyl, mercapto, primary and/or secondary amino groups, having a number-average molar weight $M_n$ of not more than 500 g/mol, (a4) optionally at least one compound having at least two groups reactive toward isocyanate groups and selected from hydroxyl, mercapto, primary and/or secondary amino groups, having a number-average molar weight $M_n$ of more than 500 g/mol, (a5) at least one amine of the formula (III)

$$H-NR^1R^2 \qquad (III)$$

(a6) optionally at least one compound which is different from (a2) and (a5) and which has precisely one group reactive toward isocyanate groups, and (a7) optionally at least one polyisocyanate different from (a1).

2. The rheological assistant according to claim 1, wherein at least one of the two radicals $R^1$ and $R^2$ is a radical of the formula (II)

$$-R^3-R^4 \qquad (II),$$

in which

R³ is C₁ to C₁₀ alkylene, and

R⁴ is optionally substituted C₆ to C₁₂ aryl.

3. The rheological assistant according to claim 2, wherein one of the radicals R¹ and R² is hydrogen and one is a radical of the formula (II).

4. The rheological assistant according to claim 2, wherein precisely one of the two radicals R¹ and R² is a radical of the formula (II), in which R³ is methylene and R⁴ is unsubstituted C₆ to C₁₂ aryl, and (a2) is at least one compound having precisely one group reactive toward isocyanate groups, and at least one free-radically polymerizable C=C double bond.

5. A process for preparing a rheological assistant according to claim 1, which comprises reacting at least one compound which has at least one isocyanate-reactive group and at least one (meth)acrylate group with at least one polyisocyanate based on aliphatic and/or cycloaliphatic diisocyanates, the polyisocyanate comprising an isocyanato acrylate containing allophanate group and optionally further synthesis components in such a way that on average per molecule there still remains at least one free isocyanate group, and reacting this at least one free isocyanate group with an amine of the formula (III)

H—NR¹R²                    (III).

6. The process according to claim 5, wherein the amine of the formula (III) is selected from the group consisting of anilines, benzylamines, substituted benzylamines, optically active amines, and 9-aminofluorene.

7. The process according to claim 5, wherein the amine of the formula (III) is selected from the group consisting of N-methylbenzylamine, N-ethylbenzylamine, N-isopropylbenzylamine, N-phenylbenzylamine, dibenzylamine, 2-methoxybenzylamine, 2-chlorobenzylamine, 4-fluorobenzylamine, 4-methylbenzylamine, 4-methoxybenzylamine, 3-(trifluoromethyl)benzylamine, 2,6-difluorobenzylamine, 3,4-dichlorobenzylamine, N-benzyl-2-phenethylamine, 1-naphthylmethylamine, 4-hydroxy-3-methoxybenzylamine (vanillylamine), 1,2,3,4-tetrahydroisoquinoline, and phenethylamine.

8. The rheological assistant according to claim 1, wherein the amine of the formula (III) is selected from the group consisting of anilines, benzylamines, substituted benzylamines, optically active amines, and 9-aminofluorene.

9. The rheological assistant according to claim 1, wherein the amine of the formula (III) is selected from the group consisting of N-methylbenzylamine, N-ethylbenzylamine, N-isopropylbenzylamine, N-phenylbenzylamine, dibenzylamine, 2-methoxybenzylamine, 2-chlorobenzylamine, 4-fluorobenzylamine, 4-methylbenzylamine, 4-methoxybenzylamine, 3-(trifluoromethyl)benzylamine, 2,6-difluorobenzylamine, 3,4-dichlorobenzylamine, N-benzyl-2-phenethylamine, 1-naphthylmethylamine, 4-hydroxy-3-methoxybenzylamine(vanillylamine), 1,2,3,4-tetrahydroisoquinoline, and phenethylamine.

10. A radiation-curable coating composition comprising
at least one rheological assistant according to claim 1,
at least one reactive diluent, and
optionally at least one photoinitiator.

11. The radiation-curable coating composition according to claim 8, wherein the amount of urea group of the formula (1) is at least 0.03 mol of urea group of the formula (1) per kg of the sum total of rheological assistant and reactive diluent.

12. The radiation-curable coating composition according to claim 10, wherein the reactive diluent is selected from the group consisting of urethane(meth)acrylates, epoxy(meth)acrylates, polyether(meth)acrylates, polyester(meth)acrylates and polycarbonate(meth)acrylates.

13. A process for producing a radiation-curable coating composition according to claim 10, which comprises preparing the rheological assistant in at least part of the at least one reactive diluent and mixing the product with the optionally at least one photoinitiator.

14. A process for coating a substrate selected from the group consisting of metal, wood, paper, ceramic, glass, plastic, textile, leather, nonwoven, and mineral building materials, comprising coating the substrate with the coating composition according to claim 10.

15. A process for regulating the viscosity of a radiation-curable coating composition, comprising adding the rheological assistant according to claim 1 to the radiation-curable coating composition.

* * * * *